United States Patent [19]

Binder et al.

[11] Patent Number: 4,812,472

[45] Date of Patent: Mar. 14, 1989

[54] ISOXAZOLE COMPOUNDS AND PHARMACEUTICAL COMPOSITIONS CONTAINING THEM FOR TREATMENT AND PROPHYLAXIS OF RETROVIRUSES DISEASES

[75] Inventors: Dieter Binder, Vienna; Franz Rovenszky, Bruck an der Leitha, both of Austria

[73] Assignee: Chemie Linz Akteingesellschaft, Linz, Austria

[21] Appl. No.: 120,264

[22] Filed: Nov. 12, 1987

Related U.S. Application Data

[63] Continuation-in-part of Ser. No. 864,606, May 19, 1986, abandoned.

[30] Foreign Application Priority Data

May 17, 1985 [AT] Austria .................................. 1493/85

[51] Int. Cl.[4] .................... A61K 31/42; C07D 413/14; C07D 409/14
[52] U.S. Cl. .................................. 514/374; 548/237; 548/238
[58] Field of Search ................ 548/237, 238; 514/374

[56] References Cited

U.S. PATENT DOCUMENTS 2,714,082  7/1955  Davies et al. ...................... 548/237

Primary Examiner—Donald G. Daus
Assistant Examiner—Cecilia Shen
Attorney, Agent, or Firm—Wenderoth, Lind & Ponack

[57] ABSTRACT

Substituted isoxazole derivatives of the formula

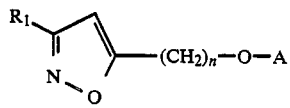

in which $R_1$ denotes lower alkyl, n denotes the integer 6, 7 or 8, A denotes a group of the formula

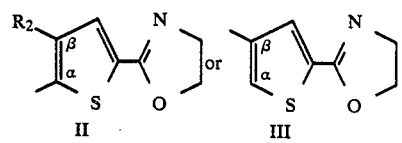

and $R_2$ denotes hydrogen, methyl, chlorine or bromine. The novel compounds have a pronounced antiviral action and can be employed for the treatment and prophylaxis of virus diseases.

6 Claims, No Drawings

ISOXAZOLE COMPOUNDS AND PHARMACEUTICAL COMPOSITIONS CONTAINING THEM FOR TREATMENT AND PROPHYLAXIS OF RETROVIRUSES DISEASES

This application is a continuation in part of Ser. No. 864,606, filed May 19, 1986, now abandoned.

The invention relates to novel substituted isoxazole derivatives of the formula

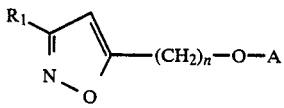

in which $R_1$ denotes lower alkyl, n denotes the integer 6, 7 or 8, A denotes a group of the formula

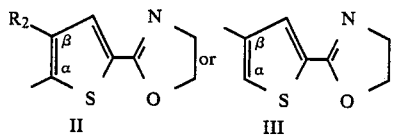

and $R_2$ denotes hydrogen, methyl, chlorine or bromine, a process for their preparation, pharmaceutical products containing these compounds and their use.

The expression "lower alkyl" used in this description means straight-chain or branched hydrocarbon groups with 1 to 4 carbon atoms, such as, for example, methyl, ethyl, propyl, isopropyl, butyl or tert.-butyl.

In a preferred group of compounds of the formula I, $R_1$ denotes methyl or ethyl, methyl being particularly preferred. $R_2$ is preferably hydrogen and n preferably represents the number 7.

A particularly preferred group within the compounds of the general formula I is that in which A denotes a 5-(4,5-dihydro-2-oxazolyl)-thienyl group of the formula II bonded to the isoxazolyl-alkoxy radical in the alpha-position to the sulfur atom.

Particularly preferred individual compounds are 5-(7-(5-(4,5-dihydro-2-oxazolyl)-2-thienyl)oxyheptyl)-3-methyl-isoxazole and 5-(7-(2-(4,5-dihydro-2-oxazolyl)-4-thienyl)oxyheptyl)-3-methyl-isoxazole.

The isoxazole derivatives of the formula I can be prepared according to the invention by cyclizing a compound of the formula

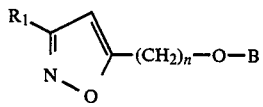

in which $R_1$ and n are as defined above, B denotes a group of the formula

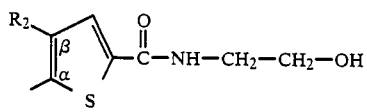

or

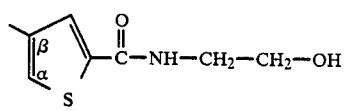

and $R_2$ is as defined above, by treatment with a dehydrating reagent, to form the oxazole ring.

The reaction according to the invention can be carried out in the presence or absence of an inert organic solvent.

If the reaction is carried out in the presence of a solvent, examples of suitable solvents are hydrocarbons, such as benzene, toluene or xylene, halogenated hydrocarbons, such as chloroform, chlorobenzene, methylene chloride or carbon tetrachloride, ethers, such as dioxane, tetrahydrofuran, dimethylformamide and the like, or mixtures of such solvents. Possible dehydrating agents here are the reagents usually employed for such cyclization reactions, for example phosphorus oxychloride, phosphorus pentachloride, thionyl chloride and the like. The dehydrating reagent can be employed for this in equivalent amounts or in a slight excess, for example in amounts of 1.1 to 3 mol per mol of the compound of the formula IV. The reaction is carried out at −20° C. to +10° C., preferably at −5° C. to +5° C.

In a particularly preferred embodiment of the process according to the invention, the compounds of the general formula IV are in general cyclized in the absence of a separate solvent by treatment with an excess of a liquid dehydrating reagent, which in this case simultaneously serves as the solvent, at −30° C. to +10° C., preferably −5° C. to +5° C. and especially preferably in an icebath at about 0° C. Suitable reagents for this purpose are again phosphorus oxychloride or thionyl chloride, the use of thienyl chloride having proved to be especially advantageous.

The starting compounds of the general formula IV used for the process according to the invention can be prepared in a manner which is known per se, starting from known products. In particular, the starting compounds can be synthesized in accordance with the following equation and the specific statements in the examples.

In the following equation, $R_1$ and n have the same meaning as in formula I. According to the reaction sequence shown in the equation, both compounds of the general formula IV in which B denotes a group of the formula V and compounds of the general formula IV in which B denotes a group of the formula VI can be synthesized. The hydroxy- or isoxazolyl-alkoxy radical is accordingly either in the alpha- or beta-position in the formulae X, XI, XIIa and XIII of the equation, and if this occupies the alpha-position, any redical $R_2$ present is bonded to the thienyl group in the beta-position.

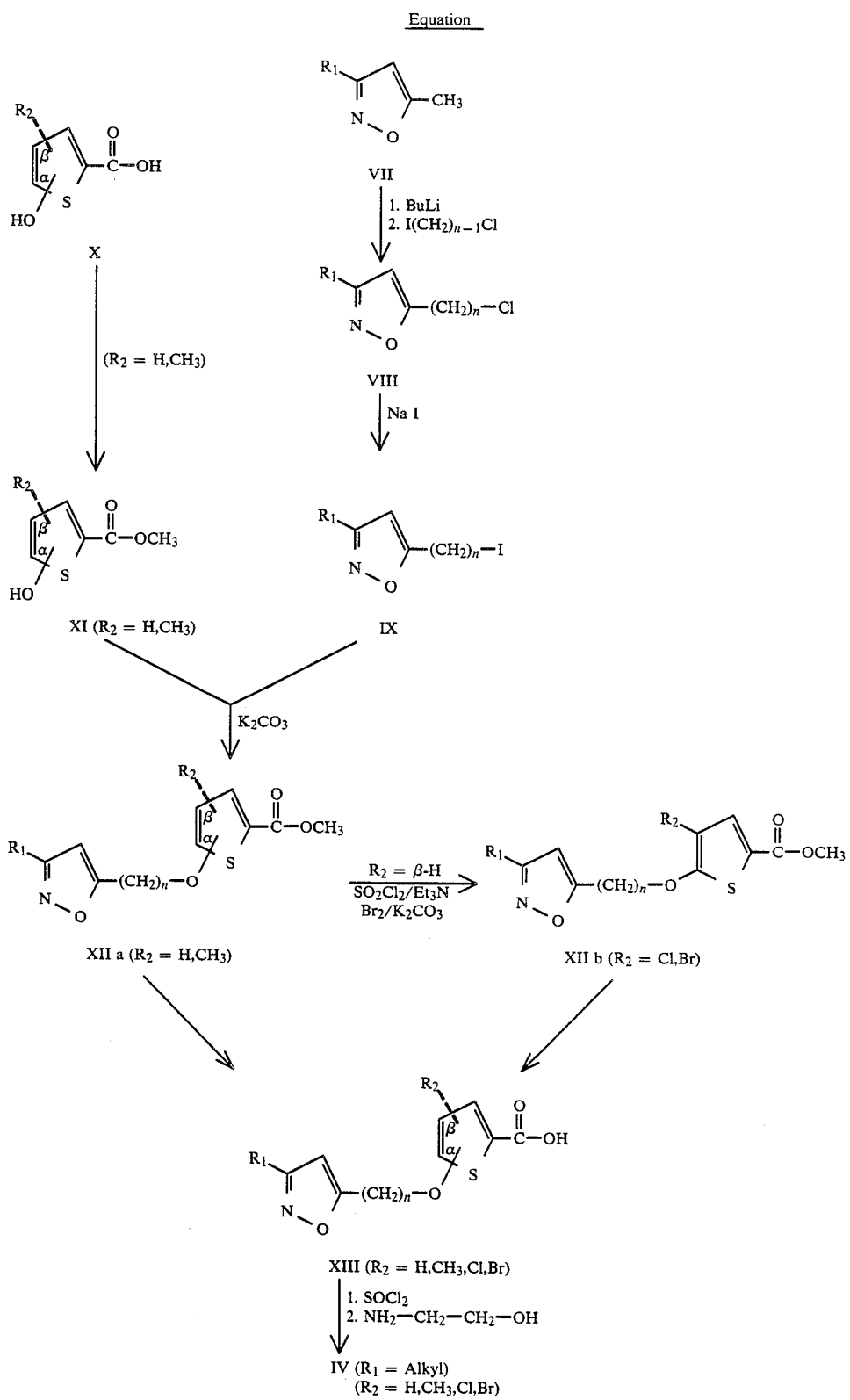

Equation

The compounds of the general formula I have an anti-infective action, and in particular a pronounced antiviral action. These useful pharmacological properties can be determined in vitro and in vivo using standard methods. The compounds of the general formula I thereby exhibit an outstanding action in particular against various types of retroviruses, as for example picornaviruses and HIV-viruses. Examples for picornaviruses are rhino- and enteroviruses, which contain echo-, coxackie- and polioviruses. The compounds of the general formula I can therefore be employed in the treatment and prophylaxis of diseases, caused by retroviruses, in mammals, especially in humans.

The following test methods were used to investigate the antiviral properties:

A: General test against different viruses:

Serial three-fold dilutions of solutions of the substances under investigation in MEM (minimum essential medium) were prepared in microtiter plates with a flat bottom. The same volumes of the particular virus dilutions in MEM and cell suspension in MEM with 15% FCS (fetal calf blood serum) were added. The cell concentration here was chosen such that a confluent cell lawn was formed after −2 days. The virus dilutions were adjusted so that a complete cytopathic effect occurred after 3–4 days, without the addition of an inhibiting substance.

As controls, cells (cell control), cells with virus (virus control) and cells with the test substances in various concentrations (toxicity control) were also run. The substance concentration at which a cell density which was still lower than in the cell control was observed was determined as the minimum toxic concentration (MTC).

The test substances were dissolved in dimethylsulfoxide and the solutions were diluted in MEM and suspended thoroughly by means of ultrasound.

The compounds according to the invention were investigated for their antiviral action in a representative cross-section of rhinoviruses of the type B1-55, echoviruses type B-9 and polioviruses type 2 and the minimum inhibotry concentration (MIC in μg/ml) was thereby determined.

In this virus inhibition test, known as a standard method, the MIC values shown in Table 1 were determined for compounds of the general formula I, such as, for example, 5-(7-(5-(4,5-dihydro-2-oxazolyl)-2-thienyl)-oxyheptyl)-3-methyl-isoxazole (compound A) or 5-(7-(2-(4,5-dihydro-2-oxazolyl)-4-thienyl)oxyheptyl)-3-methyl-isoxazole (compound B).

TABLE 1

Antiviral action in vitro of compounds of the formula I

| | | Minimum inhibitory conc. (MIC, μg/ml) | |
|---|---|---|---|
| Organism | Serotype | Compound A | Compound B |
| Rhino | type 3 | 0,03 | 0,1 |
| Rhino | type 16 | 0,3 | 1,0 |
| Rhino | type 26 | 0,3 | 1,0 |
| Rhino | type 32 | 1,0 | 3,0 |
| Rhino | type 37 | 0,03 | 0,03 |
| Rhino | type 48 | 0,1 | 1,0 |
| Rhino | type 55 | 0,3 | 0,3 |
| Echo | type B-9 | 0,03 | 1,0 |
| Polio | type 2 | 0,1 | 1,0 |
| MTC[1] | | 10 | 10 |

[1]Minimum toxic concentration

Compared with conventional compounds with antiviral properties, the compounds according to the invention have the advantage of improved lipophilic properties, which allow the blood-brain barrier to be overcome.

B: Test against HIV-virus

The anti-HIV assay for testing the anti-AIDS-activity was performed according to Mitsuya H. et al., Rapid in vitro systems for assessing activity of agents againt HTLV-III/LAV, in AIDS: Modern Concepts and Chemotherapeutic Challenges (S. Broder, ed.). Marcel Dekker, Inc., New York, 303-333 (1986):

Human T-lymphocyte-ATH8-cells were pretreated with polybrene at 2 μg/ml for 30 min at 37° C. Cells were then pelleted, suspended in fresh RPMI-1640 culture medium containing 13% fetal calf serum, 11% interleukin-2 (v/v), 50 μM β-mercaptoethanol, 4 mM L-glutamine, 50 units/ml penicillin, and 50 μg/ml streptomycin, and infected with $2 \times 10^3$ virions/cell for 60–90 min at 37° C. (The HTLV-III$_B$ viruses were derived from a pool of American patients with AIDS. Approximately $6 \times 10^{10}$ virus particles/ml were obtained from the culture supernatant of HIV-producing H9 cells as described by Mitsuya, H. et al., Proc. Natl. Acad. Sci. USA 82, 7096–7100 (1985).)

This virus concentration represents 400 times the minimum dose required to induce cytopathogenicity in ATH8 cells and, thus, represents a very high multiplicity of infection. After infection, cells were reconstituted in culture medium and seeded in culture tubes at 2 ml/tube in the presence or absence of the test compound. After incubation for 6–7 or 10 days at 37° C., the number of viable cells was counted and compared to controls without the test compound.

In this test, compound A showed a marked inhibitory effect on HIV-induced cytopathogenicity in ATH8 cells (Tab. 2). With a MIC$_{50}$ of 0,2 μMol, recorded at day 7 after infection, compound A was very potent against HIV-viruses in inhibiting the cytopathogenicity.

TABLE 2

| | Recorded at day 6-7 after virus inoculation | | | Recorded at day 10 after virus inoculation | | |
|---|---|---|---|---|---|---|
| | MIC$_{50}$[1] | ID$_{50}$[2] | ID$_{50}$/MIC$_{50}$[3] (μMol) | MIC$_{50}$ | ID$_{50}$ | ID$_{50}$/MIC$_{50}$ (μMol) |
| compound A | 0,20 | 35 | 175 | 0,20 | 35 | 175 |

[1]Concentration required to reduce virus-induced cytopatogenicity by 50%
[2]Concentration required to reduce ATH8 cell viability by 50% (compared to untreated control)
[3]The ratio ID$_{50}$/MIC$_{50}$ represents the in vitro therapeutic index.

The compounds of the general formula I can be administered by a variety of conventional routes, as for example orally and parenterally. Preferably, the compounds are administered orally. In the case of oral administration the daily dose is approximately between 0,01 and 10 mg/kg body weight, preferably, between 0,1 and 1,0 mg/kg body weight. However, at the discretion of the attending physician, some variation in dosage can occur, depending upon the condition of the subject being treated the particular compound employed, and the type of formulation used.

The dosage will be about the same for the treatment of virus diseases and for prophylaxis purposes. For prophylaxis purposes, oral administration is preferred.

The compounds of the general formula I can be used alone or in combination with other pharmaceutically active compounds. In any case, the active ingredient(s) will generally be further combined with pharmaceutically acceptable carriers or diluents. For oral use, suitable pharmaceutical carriers include innert diluents or fillers, thereby forming dosage forms such as tablets, powders, capsules, and the like. These pharmaceutical compositions can, if desired, contain additional ingredients such as flavorings, binders, excipients and the like. For example, tablets containing various excipients, such as sodium citrate, are employed, together with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials therefor include lactose or milk sugar and high molecular weiht polyehtylene glycols.

For parenteral adiministration, solution or suspension of the compounds of formula I in aqueous solutions, for example aqueous propylene glycol, sodium chloride, dextrose or sodium bicarbonate solutions are employed. Such dosage forms are suitably buffered if desired. If appropriate, they are sterilized and contain auxiliaries such as preservatives, stabilizers or emulsifiers and the like.

EXAMPLE 1

5-(7-((5-(4,5-Dihydro-2-oxazolyl)-2-thienyl)oxyheptyl)-3-methyl-isoxazole 0.60 g (1.64 mmol) of N-(2-hydroxyethyl)-5-(7-(3-methyl-5-isoxazolyl)-heptyloxy)-2-thiophenecarboxylic acid amide (IV) is introduced into 2.5 ml of thionyl chloride at 0° C., the mixture is stirred at 0° C. for 15 minutes and the excess thionyl chloride is then removed in vacuo. The residue is partitioned between saturated sodium bicarbonate solution and ethyl acetate. The mixture is extracted twice more with ethyl acetate and the combined organic phases are dried over sodium sulfate/active charcoal and evaporated.

The crude product (0.52 g of yellowish crystals) is purified by column chromatography (1:35, silica gel 60, particle size 0.040–0.063; eluting agent: ethyl acetate:petroleum ether=3:1).

Yield, 0.29 g of colorless crystals (50.7% of theory).
Melting point=69°–70° C. (diisopropyl ether).

The starting material can be prepared as follows:

5-(7-Chloroheptyl)-3-methyl-isoxazole (VIII)

21.0 g (0.216 mol) of 3,5-dimethylisoxazole (VII) (prepared in accordance with the method of C. Kashima et al., Bull. Chem. Soc. Jap. 46, 310, 1973) are dissolved in 200 ml of absolute tetrahydrofuran, the solution is cooled to −80° C. and 160 ml of n-butyllithium (1.35M solution in n-hexane, 0.216 mol) are added dropwise at this temperature in the course of 40 minutes. The mixture is stirred at a temperature below −75° C. for a further 15 minutes.

The reaction mixture is then added dropwise to a solution of 53.5 g (0.217 mol) of 1-iodo-6-chlorohexane (prepared in accordance with the method of W. F. Huber, J. Am. Chem. Soc. 73, 2730, 1951) in 150 ml of absolute tetrahydrofuran so that the temperature does not rise above −60° C. When the addition has ended, the mixture is stirred at −60° C. for a further 15 minutes and allowed to warm to room temperature.

The reaction mixture is partitioned between methylene chloride and 0.2N HCl, the aqueous phase is extracted three more times with methylene chloride and the combined organic phases are dried over sodium sulfate and evaporated.

The crude product (about 45 g) is distilled in portions in a bulb tube (air bath temperature 80° C./0.2 mbar).

Yield: 26.9 g of a yellowish oil.

Methyl 5-(7-(3-methyl-5-isoxazolyl)heptyloxy)-2-thiophenecarboxylate (XIIa)

9.3 g (43.1 mmol) of 5-(7-chloroheptyl)-3-methylisoxazole and 7.12 g (47.4 mmol) of sodium iodide are heated under reflux in 60 ml of absolute acetone for 24 hours. The mixture is then cooled, the NaCl which has precipitated out is filtered off with suction and washed with a little acetone, and 7.16 g (45.3 mmol) of methyl 5-hydroxy-2-thiophenecarboxylate (XI) and 13.1 g (94.8 mmol) of potassium carbonate are added to the filtrate. The mixture is heated under reflux for 2 hours, cooled and largely evaporated. The residue is partitioned between water and ether and the aqueous phase is extracted twice with ether. The combined organic phases are washed with a little saturated sodium bisulfite solution, dried over sodium sulfate/active charcoal and evaporated.

The crude product (11.9 g; 82% of theory) is recrystallized from diisopropyl ether.

Yield: 5.2 g of pale pink crystals (35.5% of theory).
Melting point 55°–56° C. (diisopropyl ether).

5-(7-(3-Methyl-5-isoxazolyl)heptyloxy)-2-thiophenecarboxylic acid (XIII)

0.98 g (2.90 mmol) of methyl 5-(7-(3-methyl-5-isoxazolyl)heptyloxy-2-thiophenecarboxylate is heated under reflux in 8 ml of ethanol and 4 ml of water, and 0.18 g (3.19 mmol) of KOH, dissolved in 6 ml of water and 4 ml of ethanol, is added dropwise to this solution in the course of 10 minutes. The mixture is then heated under reflux for a further 2.5 hours.

After cooling, the mixture is largely evaporated, the residue is partitioned between water and ether and the aqueous phase is acidified to pH 1.5 with 2N HCl. The mixture is extracted three times with a total of 80 ml of ether and the combined organic phases are dried over sodium sulfate/active charcoal and evaporated.

Yield: 0.90 g of colorless crystals (95.8% of theory).
Melting point 96°–7° C. (diisopropyl ether).

N-(2-Hydroxyethyl)-5(7-(3-methyl-5-isoxazolyl)-heptyloxy)-2-thiophenecarboxylic acid amide (IV)

2 ml of thionyl chloride are slowly added dropwise to 0.81 g (2.51 mmol) of 5-(7-(3-methyl-5-isoxazolyl)-heptyloxy)-2-thiophenecarboxylic acid, while cooling and stirring, a clear solution being formed. The solution is stirred at room temperature for a further 30 minutes and excess thionyl chloride is then removed in vacuo. The residue is dissolved in 6 ml of absolute methylene chloride, and a solution of 0.34 g (5.51 mmol) of ethanolamine in 5 ml of absolute methylene chloride is added dropwise at a temperature of 15° C. The mixture is stirred at room temperature for a further hour and concentrated somewhat and the concentrate is partitioned between water and ethyl acetate. The aqueous phase is extracted once more with a little ethyl acetate and the combined organic phases are washed with water, dried over sodium sulfate/active charcoal and evaporated.

Yield: 0.81 g of yellowish crystals (88.2% of theory).
Melting point 107°–10° C. (acetonitrile).

EXAMPLE 2

5-(7-(2-(4,5-Dihydro-2-oxazolyl)-4-thienyl)oxyheptyl)-3-methyl-isoxazole 5 ml of thionyl chloride are introduced into 2.06 g (5.62 mmol) of N-(2-hydroxyethyl)-4-(7-(3-methyl-5-isoxazolyl)-heptyloxy)-2-thiophenecarboxylic acid amide (IV) at 0° C., the mixture is stirred at 0° C. for 10 minutes and the excess thionyl chloride is then removed in vacuo, without warming. The residue is partitioned between saturated sodium bicarbonate solution and ethyl acetate. Extraction is carried out twice more with ethyl acetate and the combined organic phases are dried over sodium sulfate/active charcoal and evaporated. The crude oil is purified by column chromatography (1:40, silica gel 60, particle size 0.040 to 0.063; eluting agent: ethyl acetate:petroleum ether=3:1).

Yield: 0.52 g of yellowish crystals (26.5% of theory).
Melting point: 67°–68° C. (diisopropyl ether).
The starting material can be prepared as follows:

Methyl 4-hydroxy-2-thiophenecarboxylate (XI)

50.0 g (0.347 mol) of 4-hydroxy-2-thiophenecarboxylic acid and 58.3 g (0.694 mol) of sodium carbonate are heated to the boiling point in 990 ml of absolute 2-butanone under nitrogen, and 43.7 g (0.347 mol) of dimethyl sulfate are added dropwise in the course of 20 minutes. The mixture is heated under reflux for a further 2.5 hours. It is then evaporated in vacuo and the residue is partitioned between saturated sodium carbonate solution and ether. The aqueous phase is extracted five more times with 80 ml of ether each time. The combined organic phases are dried over sodium sulfate/active charcoal, filtered and evaporated.

Yield: 49.6 g of yellowish crystals (90%).
Melting point: 84°–85° C. (diisopropyl ether/petroleum ether).

5-(7-Iodoheptyl)-3-methyl-isoxazole (IX)

16.66 g (77.23 mmol) of 5-(7-chloroheptyl)-3-methyl-isoxazole (VIII) and 12.75 g (85.06 mmol) of sodium iodide NaI are heated under reflux in 110 ml of anhydrous acetone. A $^1$H—NMR shows a conversion of about 85% after 7 hours and about 89% after 22 hours. After 27 hours, the mixture is concentrated and the residue is partitioned between methylene chloride and water (with the addition of a few ml of 2N hydrochloric acid). The aqeuous phase is extracted by shaking several times with a total of 250 ml of methylene chloride and the organic phase is dried over sodium sulfate and evaporated.

Yield: 22.95 g of a brown liquid (96.7% of theory).

Methyl 4-(7-(3-methyl-5-isoxazolyl)-heptyloxy)-2-thiophenecarboxylate (XIIa)

6.42 g (40.60 mmol) of methyl 4-hydroxy-2-thiophenecarboxylate (XIa) and 11.88 g (38.67 mmol) of 5-(7-iodoheptyl)-3-methyl-isoxazole (IX) are heated under reflux with 5.34 g (40.60 mmol) of potassium carbonate ($K_2CO_3$) in 130 ml of anhydrous acetone for 8 hours. After the mixture has been left to stand overnight, it is concentrated, the residue is partitioned between 2N NaOH and ether and the aqueous phase is extracted several times with a total of 150 ml of ether. The organic phase is dried over sodium sulfate/active charcoal and evaporated.

Yield: 12.56 g of yellow crystals (96.3% of theory).
Melting point=58°–60° C.

4-(7-(3-Methyl-5-isoxazolyl)-heptyloxy)-2-thiophenecarboxylic acid (XIII)

11.34 g (33.61 mmol) of methyl 4-(7-(3-methyl-5-isoxazolyl)-heptyloxy)-2-thiophenecarboxylate are heated under reflux in 95 ml of ethanol and 45 ml of water, and 2.18 g (38.9 mmol) of KOH, dissolved in 70 ml of water and 46 ml of ethanol, are added dropwise to this solution. After the mixture has been heated under reflux for 3 hours, it is cooled and concentrated, the residue is partitioned between water and ether and the aqueous phase, after acidification to pH 1 with 2N HCl, is extracted several times with ether. The combined organic phases are dried over sodium sulfate/active charcoal and evaporated.

Yield: 9.28 g of yellow crystals (85.6% of theory).
The crude product can be used directly in the next stage or can be recrystallized from diisopropyl ether, colorless crystals being obtained.
Melting point=110°–13° C.

N-(2-Hydroxyethyl)-4-(7-(3-methyl-5-isoxazolyl)-heptyloxy)-2-thiophenecarboxylic acid amide (IV)

About 15 ml of thionyl chloride are added to 5.3 g (16.44 mmol) of 4-(7-(3-methyl-5-isoxazolyl)-heptyloxy)-2-thiophenecarboxylic acid at 0° C. and the mixture is stirred at room temperature for 20 minutes. After filtration with suction under a waterpump vacuum, the residue is taken up in 40 ml of anhydrous methylene chloride and a solution of 2.2 g (36.09 mmol) of ethanolamine in 40 ml of anhydrous methylene chloride is added dropwise, with cooling. After the mixture has been stirred at room temperature for 2 hours, it is cooled and partitioned between water and methylene chloride, about 2N HCl being added for better separation of the phases. After shaking back the two phases, the organic phase is dried over sodium sulfate/active charcoal and evaporated.

Yield: 5.74 g of brown crystals (95.6% of theory).
Melting point: 56°–57° C. (crude product, can be used directly, without losses in yield, for the preparation of the compound of the formula I).

What we claim is:

1. A compound of the formula

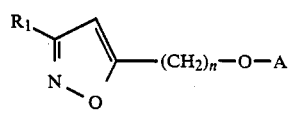

in which $R_1$ denotes lower alkyl, n denotes the integer 6, 7 or 8, A denotes a group of the formula

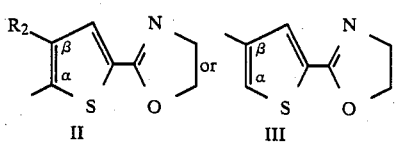

and $R_2$ denotes hydrogen, methyl, chlorine or bromine.

2. The compound of the formula I as claimed in claim 1, in which A denotes a group of the formula II.

3. The compound of the formula I as claimed in claim 1, in which $R_1$ denotes methyl and $R_2$ denotes hydrogen.

4. The compound 5-(7-(5-(4,5-dihydro-2-oxazolyl)-2-thienyl)oxyheptyl-3-methylisoxazole as claimed in claim 1.

5. The compound 5-(7-(2-(4,5-dihydro-2-oxazolyl)-4-thienyl)oxyheptyl)-3-methylisoxazole as claimed in claim 1.

6. A pharmaceutical composition for the treatment and prophylaxis of diseases, caused by different classes of retroviruses, containing a compound for formula

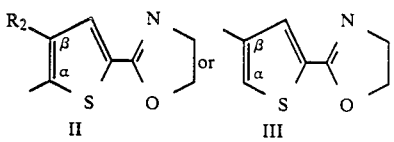

in which $R_1$ denotes lower alkyl, n denotes the integer 6, 7 or 8, a denotes a group of the formula and $R_2$ denotes hydrogen, methyl, chlorine or bromine in an amount effective for the treatment of diseases caused by different classes of retroviruses in combination with a pharmaceutically acceptable carrier or diluent.

* * * * *